United States Patent
Osumi et al.

(10) Patent No.: US 12,115,025 B2
(45) Date of Patent: Oct. 15, 2024

(54) ULTRASONIC DIAGNOSTIC SYSTEM

(71) Applicant: CANON MEDICAL SYSTEMS CORPORATION, Otawara (JP)

(72) Inventors: Ryota Osumi, Nasushiobara (JP); Takatoshi Okumura, Yaita (JP); Takeshi Sato, Nasushiobara (JP); Kentaro Kikuchi, Saitama (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 475 days.

(21) Appl. No.: 17/400,551

(22) Filed: Aug. 12, 2021

(65) Prior Publication Data

US 2022/0047248 A1 Feb. 17, 2022

(30) Foreign Application Priority Data

Aug. 14, 2020 (JP) .................. 2020-136919

(51) Int. Cl.
*G01S 1/72* (2006.01)
*A61B 8/00* (2006.01)

(52) U.S. Cl.
CPC . *A61B 8/56* (2013.01); *G01S 1/72* (2013.01)

(58) Field of Classification Search
None
See application file for complete search history.

(56) References Cited

U.S. PATENT DOCUMENTS

| | | |
|---|---|---|
| 8,721,551 B2 | 5/2014 | Tanabe |
| 10,660,607 B2 | 5/2020 | Ryu et al. |

(Continued)

FOREIGN PATENT DOCUMENTS

| | | |
|---|---|---|
| CN | 103099641 A | 5/2013 |
| CN | 106456110 A | 2/2017 |
| JP | 2009-172014 A | 8/2009 |

(Continued)

OTHER PUBLICATIONS

Combined Chinese Office Action and Search Report issued Jan. 23, 2024, in corresponding Chinese Patent Application No. 202110930177.1 (with English Translation of Category of Cited Documents) citing document 15 therein, 25 pages.

(Continued)

*Primary Examiner* — Walter L Lindsay, Jr.
*Assistant Examiner* — Geoffrey T Evans
(74) *Attorney, Agent, or Firm* — Oblon, McClelland, Maier & Neustadt, L.L.P.

(57) ABSTRACT

In one embodiment, an ultrasonic diagnostic system includes: a plurality of probes; at least one operation/display panel configured to be disposed at a same examination location as at least one of the plurality of probes; communication equipment configured to communicate with the plurality of probes and the operation/display panel; a measurement circuit configured to measure physical quantity related to the plurality of probes; processing circuitry configured to associate a specific probe of the plurality of probes with the operation/display panel based on the measured physical quantity; and an ultrasonic server configured to be disposed at a location different from the examination location, receive first data acquired by the specific probe via the communication equipment, generate second data based on the first data, and transmit the second data to the operation/display panel via the communication equipment.

19 Claims, 12 Drawing Sheets

(56) References Cited

U.S. PATENT DOCUMENTS 10,835,206 B2 11/2020 Bell et al.
2017/0071570 A1 3/2017 Jumatsu

FOREIGN PATENT DOCUMENTS

| JP | 2012-90712 A | 5/2012 |
| JP | 2014-57631 A | 4/2014 |
| JP | 2017-531455 A | 10/2017 |
| JP | 2018-527054 A | 9/2018 |

OTHER PUBLICATIONS

Office Action issued Feb. 13, 2024, in corresponding Japanese Patent Application No. 2020-136919 (with English Translation), citing document 16 therein, 4 pages.

ULTRASONIC DIAGNOSTIC SYSTEM

CROSS-REFERENCE TO RELATED APPLICATION

This application is based upon and claims the benefit of priority from Japanese Patent Application No. 2020-136919, filed on Aug. 14, 2020, the entire contents of which are incorporated herein by reference.

FIELD

Disclosed embodiments relate generally to an ultrasonic diagnostic system.

BACKGROUND

An ultrasonic diagnostic apparatus transmits an ultrasonic pulse or an ultrasonic continuous wave, which is generated by transducers included in an ultrasonic probe, into an object's body. Then, the ultrasonic diagnostic apparatus converts reflected ultrasonic signals, which are caused by difference in acoustic impedance between tissues inside the object, into an electric signal so as to non-invasively acquire information inside the object. A medical examination using an ultrasonic diagnostic apparatus can readily generate and acquire medical images such as tomographic images and/or three-dimensional images of areas inside an object by bringing the ultrasonic probe into contact with the body surface, and thus, is widely applied to morphological diagnosis and functional diagnosis of an organ.

An ultrasonic diagnostic system is proposed, in which an ultrasonic probe and the components excluding the ultrasonic probe (hereinafter, referred to as a "main body") are wirelessly connected. In the proposed ultrasonic diagnostic system, a cable for connecting the ultrasonic probe to the main body is not required, and thus, operability is improved. However, in the conventional proposed system, it is required to install the main body at each examination location, for example, in every examination room in a hospital. Thus, it is uneconomical when the number of patients is small. To avoid such disadvantage, the main body must be moved to the examination room where the patient is. In addition, when performing ultrasonic examination in an inpatients ward, the main body must be moved to the inpatients ward, or when ultrasonic examination is required during surgery, the main body must be moved to the operating room as well.

DETAILED DESCRIPTION

In one embodiment, an ultrasonic diagnostic system includes: a plurality of probes; at least one operation/display panel configured to be disposed at a same examination location as at least one of the plurality of probes; communication equipment configured to communicate with the plurality of probes and the operation/display panel; a measurement circuit configured to measure physical quantity related to the plurality of probes; processing circuitry configured to associate a specific probe of the plurality of probes with the operation/display panel based on the measured physical quantity; and an ultrasonic server configured to be disposed at a location different from the examination location, receive first data acquired by the specific probe via the communication equipment, generate second data based on the first data, and transmit the second data to the operation/display panel via the communication equipment.

Hereinafter, embodiments of the present invention will be described by referring to the accompanying drawings.

First Embodiment

Figure 1:
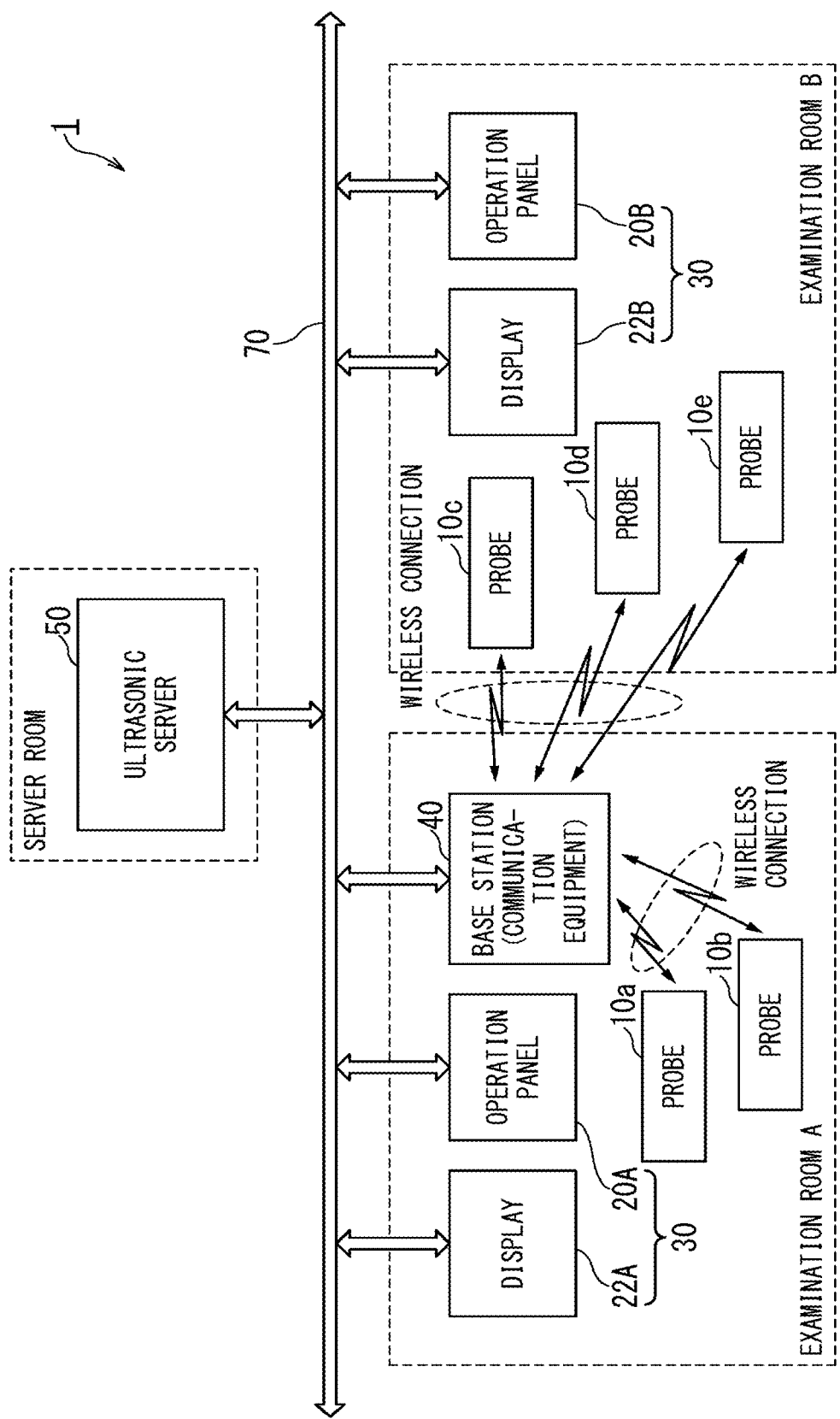
FIG. 1 is a schematic diagram illustrating a system configuration of the ultrasonic diagnostic system according to the first embodiment.

FIG. 1 is a schematic diagram illustrating a system configuration of the ultrasonic diagnostic system 1 according to the first embodiment. The ultrasonic diagnostic system 1 includes a plurality of ultrasonic probes 10 (hereinafter, simply referred to as probes 10), at least one operation/display panel 30, a base station 40 (also referred to as communication equipment 40), and an ultrasonic server 50.

The operation/display panel 30 includes an operation panel 20 and a display 22. In the case shown in FIG. 1, the operation panel 20A and the display 22A are disposed in the examination room A, and the operation panel 20B and the display 22B are disposed in the examination room B.

The operation panel 20A is provided with a trackball, various switches, and dials. Further, the operation panel 20 may include a touch panel. The touch panel is configured such that the user can input various data and information depending on the display contents on the screen by touching the panel surface. The display 22 is, for example, a display device including a liquid crystal panel and/or an organic EL (Electro Luminescence) panel.

Of the plurality of probes 10, at least one probe 10 is disposed at the same examination location as the operation panel 20 and the display 22. An example of an examination location is an examination room A or an examination room B in a hospital, as illustrated in FIG. 1. However, the examination location is not limited to these rooms. Any place where an examination or diagnosis using an ultrasonic image is conducted can be an examination location. For example, the examination location may be a consultation room in a hospital or a hospital room in which a patient is hospitalized.

In the case shown in FIG. 1, among the five probes 10 including the probes 10a, 10b, 10c, 10d, and 10e, the probes 10a and 10b are disposed in the examination room A, and the probes 10c, 10d, and 10e are disposed in the examination room B.

The communication equipment 40 (or base station 40) is located near the examination location. Although the communication equipment 40 is disposed in the examination room A in the case shown in FIG. 1, aspects of the present embodiment are not limited to such a case. For example, the communication equipment 40 may be disposed in the examination room B, or may be disposed even at a location other than the examination room A and the examination room B. The point is that the communication equipment 40 can be disposed at a location where the communication equipment 40 can communicate with the respective probes 10.

Although the communication between the communication equipment 40 and the respective probes 10 may be wireless as shown in FIG. 1, aspects of the present embodiment are not limited to such a case. The communication between the communication equipment 40 and the respective probes 10 may be performed via wired communication. In the following description, it is assumed that the communication between the communication equipment 40 and the respective probes 10 is wirelessly performed.

When the communication between the communication equipment 40 and the respective probes 10 is wirelessly performed, various communication methods can be adopted as wireless communication. For example, among wireless communication methods called 5th generation mobile communication system (so-called 5G system), the communication method called "local 5G" can be applied to the wireless communication between the communication equipment 40 and the respective probes 10. While a general 5G system is a uniform communication service developed nationwide by a specific telecommunications carrier so-called a carrier, the "local 5G" is a system in which a local government or general private companies take an initiative in building, operating, and using an independent 5G network in a specific area such as their own building and their own premises. When the communication between the communication equipment 40 and the respective probes 10 is performed by wireless communication under the local 5G, the communication equipment 40 serves as a base station and each probe 10 serves as a terminal.

Besides this, wireless LAN communication based on the IEEE 802.11 standard, so-called Wi-Fi (registered trademark) system, or an ultra-wideband wireless system called UWB (Ultra-Wide-Band) may be used for the wireless communication between the communication equipment 40 and the respective probes 10. Note that Wi-Fi of IEEE802.11ay that is the next-generation standard is said to aim for ultra-high-speed communication of 100 Gbps.

Among the signals of each probe 10, ultra-high-speed is required for the ultrasonic signals, but not necessarily required for signals for controlling each probe 10. Thus, for communication of ultrasonic signals, the above-described ultra-high-speed communication method such as the local 5G may be adopted. On the other hand, for communication of probe-control signals, a relatively low-speed communication method such as Bluetooth (registered trademark) may be adopted.

The ultrasonic server 50 may be installed at a location different from the examination locations such as the examination room A and the examination room B. For example, the ultrasonic server 50 may be installed in a predetermined server room in a hospital. The communication equipment 40 and the ultrasonic server 50 are connected via, for example, a network 70 in a hospital. The network 70 in the hospital can be configured as a wired network or as a wireless network such as the above-described local 5G.

The ultrasonic server 50 can also be installed far away from the building where the examination locations are. In this case, the network 70 shown in FIG. 1 are composed of an in-hospital network and another network that is a wired or wireless high-speed network other than the in-hospital network.

The operation panel 20A and display 22A disposed in the examination room A as well as the operation panel 20B and display 22B disposed in the examination room B are also connected to the ultrasonic server 50 via the network 70.

When the plurality of probes 10 and the plurality of operation/display panels 30 (i.e., operation panels 20 and displays 22) are connected to the network 70, the ultrasonic server 50 determines one specific probe 10 from the plurality of probes 10 and associates this specific probe 10 with one operation/display panel 30 that is appropriate for being connected to this specific probe 10, as described below. Further, the ultrasonic server 50 establishes communication between the specific probe 10 and the operation/display panel 30 associated with this specific probe 10.

After that, the ultrasonic server 50 receives the first data (for example, ultrasonic data) acquired by the specific probe 10 via the communication equipment 40 and generates the second data (for example, ultrasonic image data) on the basis of the received first data. Further, the ultrasonic server 50 sends the generated second data to the display 22 of the operation/display panel 30 associated with the specific probe 10 via the communication equipment 40, and then causes this display 22 to display an ultrasonic image based on the second data (for example, ultrasonic image data).

Figure 2:
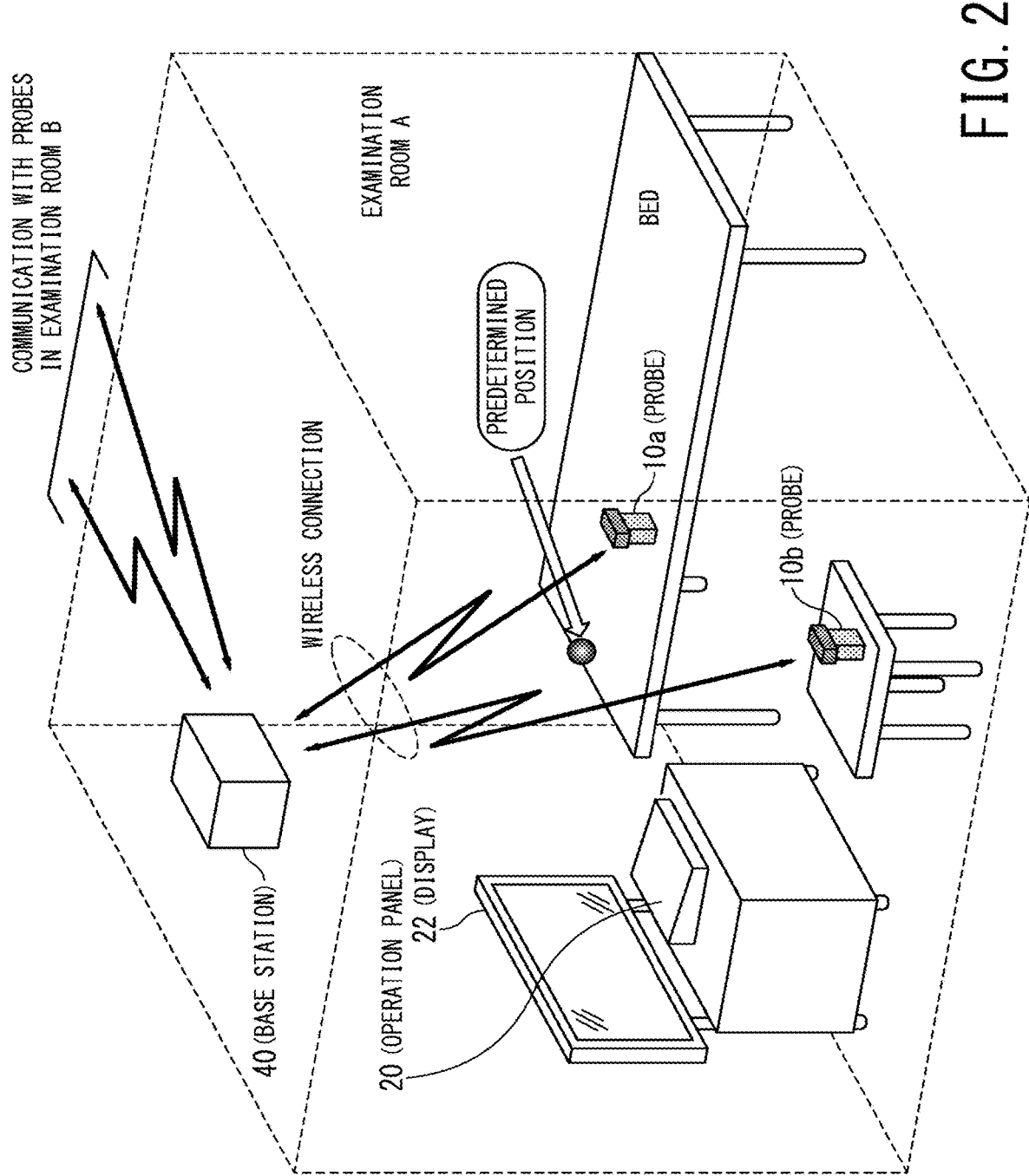
FIG. 2 is a schematic diagram illustrating disposition of components in an examination room.

FIG. 2 is a schematic diagram illustrating disposition of the above-described components in the examination room A. In the examination room A, a bed for an object (for example, a patient to be examined) to lie down is disposed. On the left side of the bed, the operation panel 20 operated by a user such as a doctor and/or an ultrasonic examination technologist and the display 22 for displaying ultrasonic images are disposed. The communication equipment 40 (for example, a base station 40) is installed in a predetermined place in the examination room A, for example, on the wall in the corner of the examination room A.

In FIG. 2, a virtual sphere is shown to indicate the predetermined position in the examination room. In the case of FIG. 2, the position of the pillow on the bed on which the patient lies down during the examination is set as the "predetermined position". Besides that, the predetermined position may be any one of the positions of the display 22, the position of the operation panel 20, and the position of the object in the examination location.

The probe 10a and the probe 10b are wirelessly connected to the communication equipment 40, and thus, can be placed at any positions in the examination room A, and also can be moved to any position. For example, in the state shown in FIG. 2, the probe 10a is disposed on a place close to the predetermined position on the bed, and the probe 10*b* is disposed on a table away from the bed.

The above-described "predetermined position" is used to determine the specific probe 10 among the plurality of probes 10 that are disposed to be able to communicate with the communication equipment 40, as described below. In the case shown in FIG. 2, one specific probe 10 is determined among the probes 10*a* and 10*b* disposed in the examination room A, and the probes 10*c*, 10*d*, and 10*e* disposed in the examination room B.

Figure 3:
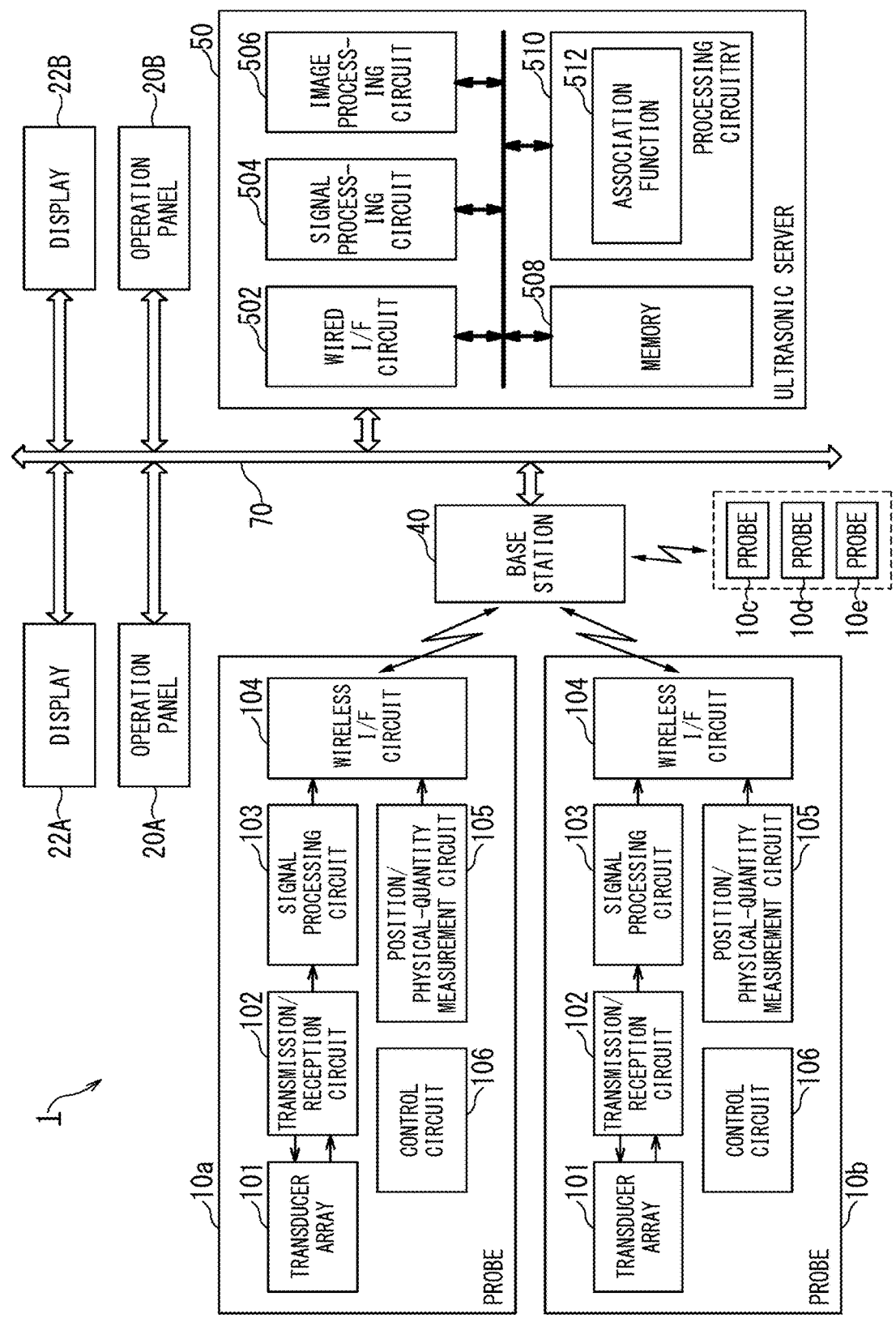
FIG. 3 is a block diagram illustrating a functional configuration of the ultrasonic diagnostic system according to the first embodiment.

FIG. 3 is a block diagram illustrating a functional configuration of the ultrasonic diagnostic system 1 according to the first embodiment. Each of the plurality of probes 10, for example, the probes 10*a* and 10*b* in the examination room A, and the probes 10*c*, 10*d*, and 10*e* in the examination room B are wirelessly connected to the base station 40 (i.e., communication equipment 40). Meanwhile, the base station 40 is connected to the ultrasonic server 50 via the network 70.

The operation panel 20A and display 22A in the examination room A as well as the operation panel 20B and display 22B in the examination room B are also connected to the ultrasonic server 50 via the network 70.

Each probe 10 includes, for example, a transducer array 101, a transmission/reception circuit 102, a signal processing circuit 103, a wireless I/F (Interface) circuit 104, a position/physical-quantity measurement circuit 105, and a control circuit 106.

The transducer array 101 is, for example, configured as an array of a plurality of transducers and includes a number of transmission channels and reception channels which respectively corresponding to the number of transducers. The transducer array 101 converts the transmission signal applied as an electrical signal to each transmission channel via the transmission/reception circuit 102 into an ultrasonic signal, transmits the ultrasonic signal to the object, receives an ultrasonic reflection signal reflected from the object, converts the ultrasonic reflection signal into an electric signal, and outputs the converted electric signal to each reception channel.

The transmission/reception circuit 102 includes, for example, a transmission circuit, a transmission/reception separation circuit, a high-voltage switch, an amplifier, an A/D converter, and a reception buffer memory.

The transmission circuit in the transmission/reception circuit 102 generates transmission signals for the respective transmission channels and outputs the transmission signals to the transmission/reception separation circuit. In the transmission circuit, a delay time is added to each of the transmission signals to be transmitted from the transducer array 101. Thereafter, the plurality of transmission signals generated in the transmission circuit are outputted to the corresponding transmission channels, and are applied to the respective elements of the transducer array 101 via the transmission/reception separation circuit and the high-voltage switch. Since a delay time is added to each transmission signal of the transmission channel, the transducer array 101 transmits an ultrasonic signal in which an ultrasonic transmission beam having directivity is formed.

An amplifier in the transmission/reception circuit 102 amplifies the reception signal acquired for each reception channel, and outputs each amplified signal to the A/D converter. The A/D converter performs A/D conversion on the analog RF (radio frequency) reception signal for each reception channel outputted from the amplifier so as to convert it into a digital RF reception signal. The digital RF reception signal for each reception channel after the A/D conversion is stored in the reception buffer memory.

The signal processing circuit 103 includes a beamformer and a data compression circuit. The beamformer applies beamforming to the reception signals stored in the reception buffer memory of the transmission/reception circuit 102. The beamformer may apply a conventional beamforming in which a reception delay time for each reception channel is added to each reception signal, and subsequently these reception signals are coherently synthesized. Alternatively, the beamformer may apply an "adaptive beamforming" in which delay-time correction is performed depending on the sound velocity distribution inside the object. Beamforming may be performed on the ultrasonic server 50, and in this case, beamforming on the signal processing circuit 103 is omitted. The data compression circuit compresses the ultrasonic reception signals before or after beamforming (hereinafter, referred to as ultrasonic data or first data) in such a manner that the wireless communication rate of the compressed data does not exceed the maximum communication rate achieved by the system.

The wireless I/F circuit 104 converts the pre-beamforming or post-beamforming ultrasonic data acquired from the signal processing circuit 103 into a wireless signal that conforms to wireless communication standards, such as the local 5G system standards, and sends the wireless signal to the base station 40. In addition to ultrasonic data, the wireless I/F circuit 104 sends signals and data necessary for the processing in the ultrasonic server 50 to the base station 40.

The position/physical-quantity measurement circuit 105 is a circuit that measures physical quantity associated with the probe (for example, the own position of the probe). The physical quantity data measured by the position/physical-quantity measurement circuit 105 are also sent to the base station 40 via the wireless I/F circuit 104 together with the ultrasonic reception signal. More detailed operation of the position/physical-quantity measurement circuit 105 will be described below.

The control circuit 106 is a circuit having a processor that controls the transmission/reception circuit 102, the signal processing circuit 103, and the wireless I/F circuit 104.

The base station 40 is the communication equipment 40 that relays each probe 10 to the ultrasonic server 50. The pre-beamforming or post-beamforming ultrasonic data outputted from the signal processing circuit 103, the physical quantity data such as the position of each probe outputted from the position/physical-quantity measurement circuit 105, and signals and data necessary for the processing in the ultrasonic server 50 are sent from the wireless I/F circuit 104 of each probe 10 to the base station 40. The base station 40 sends these data to the ultrasonic server 50 via the network 70.

The ultrasonic server 50 sends various control signals for the probes 10 to the base station 40 via the network 70. The base station 40 sends these various control signals to the wireless I/F circuit 104 of each probe 10. As described above, the communication between the base station 40 and each wireless I/F circuit 104 is performed by using wireless communication in accordance with the local 5G standards, for example.

The ultrasonic server 50 is a computer that processes ultrasonic data and includes, for example, a wired I/F (interface) circuit 502, a signal processing circuit 504, an image processing circuit 506, a memory 508, and processing circuitry 510.

The wired I/F circuit 502 is an interface for connecting the ultrasonic server 50 to the network 70.

The signal processing circuit 504 generates ultrasonic image data according to various imaging methods from the first data (i.e., the pre-beamforming or post-beamforming ultrasonic data) sent from the probes 10. With respect to the pre-beamforming ultrasonic data, the signal processing circuit 504 applies the above-described adaptive beamforming to the pre-beamforming ultrasonic data, and then generates the ultrasonic image data.

The signal processing circuit 504 generates the ultrasonic image data according to various imaging methods such as the B-mode method, the color Doppler method, the pulse Doppler method, the contrast-enhanced imaging method, and the elastic imaging method. The ultrasonic image data generated by the signal processing circuit 504 are, for example, one-dimensional ultrasonic image data in which pixel data corresponding to the adopted imaging method are arranged in the distance direction (i.e., depth direction of the object), two-dimensional ultrasonic image data in which the pixel data are arranged in the distance direction and the azimuth direction, or three-dimensional ultrasonic image data in which the pixel data are arranged in the distance direction, the azimuth direction, and the elevation direction.

The image processing circuit 506 converts the ultrasonic image data generated by the signal processing circuit 504 into a data array to generate a display image suitable for display on the display 22.

The image processing circuit 506 further generates data indicating the display position of the ultrasonic image, various auxiliary data displayed on the display 22 together with ultrasonic images, data that assist user operation, and various data of characters, figures, and diagrams for displaying data related to patient information, and then, synthesize these data into the ultrasonic image data so as to generate the second data (i.e., ultrasonic image data for display).

The ultrasonic image data for display generated by the image processing circuit 506 are converted by the wired I/F circuit 502 into a format suitable for transmission in the network 70, and then are transmitted to the display 22.

The memory 508 can store the ultrasonic image data generated by the signal processing circuit 504 and the ultrasonic image data for display generated by the image processing circuit 506. The memory 508 stores, for example, diagnostic information such as patient ID and doctor's findings, and various data such as diagnostic protocols and various body marks. When the processing performed by the signal processing circuit 504 and/or the image processing circuit 506 involves software processing, the memory 508 can store the programs required for the software processing. Further, the memory 508 stores various programs executed by the processor included in the processing circuitry 510. The memory 508 is a storage medium including an external storage device such as a HDD (Hard Disk Drive) and/or an optical disk device in addition to a ROM (Read Only Memory) and a RAM (Random Access Memory).

The processing circuitry 510 is a circuit including a processor that implements a function as an information processing device, and controls the entire processing of the ultrasonic server 50. For example, the processing circuitry 510 comprehensively controls the processing of the ultrasonic server 50 on the basis of various data, various control programs, and various setting requests inputted by an operator via the operation panel 20.

The processing circuitry 510 also implements an association function 512. The association function 512 is a function of associating one specific probe 10 of the plurality of probes 10 with one operation/display panel 30 (i.e., the operation panel 20 and the display 22) on the basis of the physical quantity measured by the position/physical-quantity measurement circuit 105 of each probe 10, for example, on the basis of the position of each probe 10. Detailed description of the association function 512 will be described below.

The processing circuitry 510 is, for example, a circuit provided with a CPU and/or a special-purpose or general-purpose processor. The processor implements various functions by executing programs stored in the memory 508. The processing circuitry 510 may be configured as a hardware such as a field programmable gate array (FPGA) and an application specific integrated circuit (ASIC). The various functions described below can also be implemented by such hardware. Additionally, the processing circuitry 510 can implement the various functions by combining hardware processing and software processing based on its processor and programs.

(Association Processing)

In the ultrasonic diagnostic system 1 of the present embodiment, as shown in FIG. 1 to FIG. 3, the plurality of probes 10 and the plurality of operation/display panels 30 (i.e., operation panels 20 and displays 22) can be connected to one ultrasonic server 50. Thus, it is important to properly associate one specific probe 10 with one specific operation/display panel 30. If this association processing is not properly performed, it may cause an undesired result, for example, that an ultrasonic image is generated on the basis of ultrasonic data from an unintended or undesired probe, such as the probe 10C in the examination room B, may be displayed on the display 22A installed in the examination room A.

Figure 4:
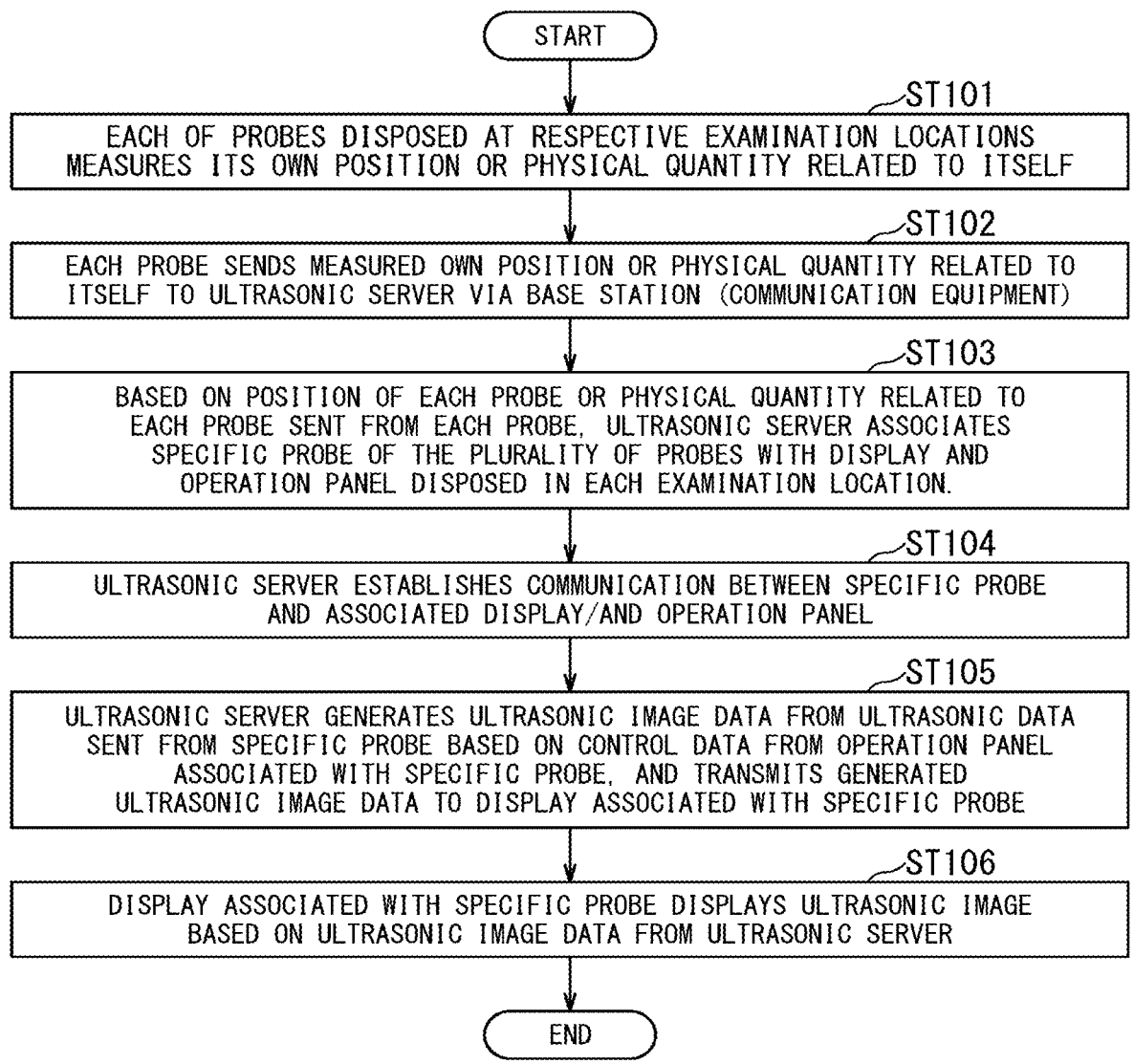
FIG. 4 is a flowchart illustrating processing performed by the ultrasonic diagnostic system according to the first embodiment.

FIG. 4 is a flowchart illustrating the processing performed by the ultrasonic diagnostic system 1 of the first embodiment, particularly focusing on the processing of associating one specific probe 10 with one specific operation/display panel 30. Hereinafter, the association processing will be described in accordance with the step number in the flowchart of FIG. 4.

In the ultrasonic diagnostic system 1 of the first embodiment, it is assumed that each of the plurality of probes 10 can be moved from one examination location to another, while each operation/display panel 30, which includes the display 22 and the operation panel 20, is fixed at a predetermined examination location. It is also assumed that the ultrasonic server 50 holds (i.e., stores) the identification information of the operation/display panel 30 installed in each examination location. For example, in the case shown in FIG. 1, it is assumed that the ultrasonic server 50 holds the identification information of the display 22A and the operation panel 20A installed in the examination room A, and holds the identification information of the display 22B and the operation panel 20B installed in the examination room B, as well.

Under these assumptions, firstly, in the step ST101, each of the plurality of probes 10 disposed at the respective examination locations measures its own position or the physical quantity related to itself.

The own position of the probe and/or the physical quantity related to itself are measured by, for example, the position/physical-quantity measurement circuit 105 in each probe 10. Alternatively, the position of each probe 10 may be measured by a separately provided measuring means.

In the next step ST102, each probe 10 sends the measured own position information or physical quantity related to itself to the ultrasonic server 50 via the base station 40.

Various methods can be used for measuring the position of each probe 10. For example, the position measurement can be achieved by using radio waves from the base station 40 (communication equipment 40) or a transmitter (not shown). Further, for example, an RSSI (Received Signal Strength Indicator) method, an AoA (Angle of Arrival) method, and a triangulation method can be used for the position measurement. With the RSSI method, each probe 10 measures its own position by using intensity of the radio wave from the base station 40 or the transmitter (not shown). With the AoA method, not only the radio-wave intensity but also the angle of the arrival direction of the radio wave are measured for determining the own position. With the triangulation method, triangulation using a plurality of transmitters is applied to the position measurement.

Besides that, the system may be configured such that a magnetic generator (not shown) is installed near the examination location and each probe 10 is provided with a magnetic sensor for measuring its own position. Further, GPS (Global Positioning System) may be used for positioning. Moreover, an acceleration sensor may be attached to each probe 10 such that each probe 10 measures its own position by using acceleration information. Still further, an optical camera may be installed in the examination room as a separately provided measuring means, and the position of each probe may be measured from the image acquired by the optical camera.

In addition, in order to improve the positioning accuracy, the above-described methods may be used in combination. The dimension of the position to be measured may be two-dimensional or three-dimensional including information in the height direction.

The position information of each probe 10 measured by the optical camera is also sent to the ultrasonic server 50 via the network 70.

Instead of directly measuring the position, the physical quantity related to each probe may be measured and then sent to the ultrasonic server 50. For example, the intensity of the radio wave from the base station 40 or the transmitter may be measured, and the measured radio-wave intensity may be sent to the ultrasonic server 50 as the physical quantity related to each probe.

In order to determine a specific probe corresponding to (i.e., associated with) the operation/display panel 30 among the plurality of probes 10, the ultrasonic server 50 may be provided with information indicating that a user such as a doctor and an ultrasonic examination technologist is actually grasping one probe 10 and is about to use this probe 10 from now on. For example, a temperature of the user's hand measured by a temperature sensor provided near the outer surface of the probe 10, and/or an acceleration information indicating vibration and position fluctuation measured by the acceleration sensor provided inside the probe 10 may be used as the physical quantity related to the probe and be sent to the ultrasonic server 50.

In the next step ST103, on the basis of the position of each probe or the physical quantity related to each probe sent from each probe 10, the ultrasonic server 50 associates one specific probe 10 of the plurality of probes 10 with the display 22 and the operation panel 20 installed in each examination location. The processing of the step ST103 is performed by the association function 512 of the ultrasonic server 50.

As described above, the ultrasonic server 50 stores the identification information of each of the display 22 and the operation panel 20 installed in each examination location. For example, the ultrasonic server 50 stores the identification information of each of the display 22A and the operation panel 20A installed in the examination room A. As shown in FIG. 2, the predetermined position is set in each examination location (for example, examination room A). For example, the predetermined position is set on the bed in examination room A.

The association function 512 of the ultrasonic server 50 selects the probe 10 closest to the predetermined position and determines it as the specific probe 10 from the plurality of probes 10, based on the position information of the respective probes 10 sent from the plurality of probes 10. For example, among the five probes 10 including the probes 10a and 10b placed in the examination room A and the probes 10c, 10d, and 10e placed in the examination room B, the probe 10a, which is closest to the predetermined position in the examination room A, is determined as the specific probe 10.

The association function 512 of the ultrasonic server 50 may determine the probe 10 closest to the predetermined position as the specific probe 10 from the plurality of probes 10, based on the physical quantities related to the respective probes 10 sent from the plurality of probes 10 (for example, intensity of a radio wave received by each probe 10).

After that, the association function 512 of the ultrasonic server 50 associates the specific probe 10, which is determined on the basis of the predetermined position at the examination location, with the display 22 and the operation panel 20 installed in the examination location.

In the next step ST104, the association function 512 of the ultrasonic server 50 establishes communication between the specific probe 10 and the associated set of the display 22 and the operation panel 20. With the establishment of this communication, for example, the display 22A and the operation panel 20A in the examination room A are connected only to the specific probe 10 closest to the predetermined position, i.e., the probe 10a.

In the next step ST105, on the basis of the control data sent from the operation panel 20 that is associated with the specific probe 10, the ultrasonic server 50 generates the ultrasonic image data from the ultrasonic data sent from the specific probe 10 and then transmits the generated ultrasonic image data to the display 22 associated with the specific probe 10.

In the next step ST106, the ultrasonic server 50 causes the display 22 associated with the specific probe 10 to display the ultrasonic image based on the ultrasonic image data.

(Modifications of First Embodiment)

Figure 5:
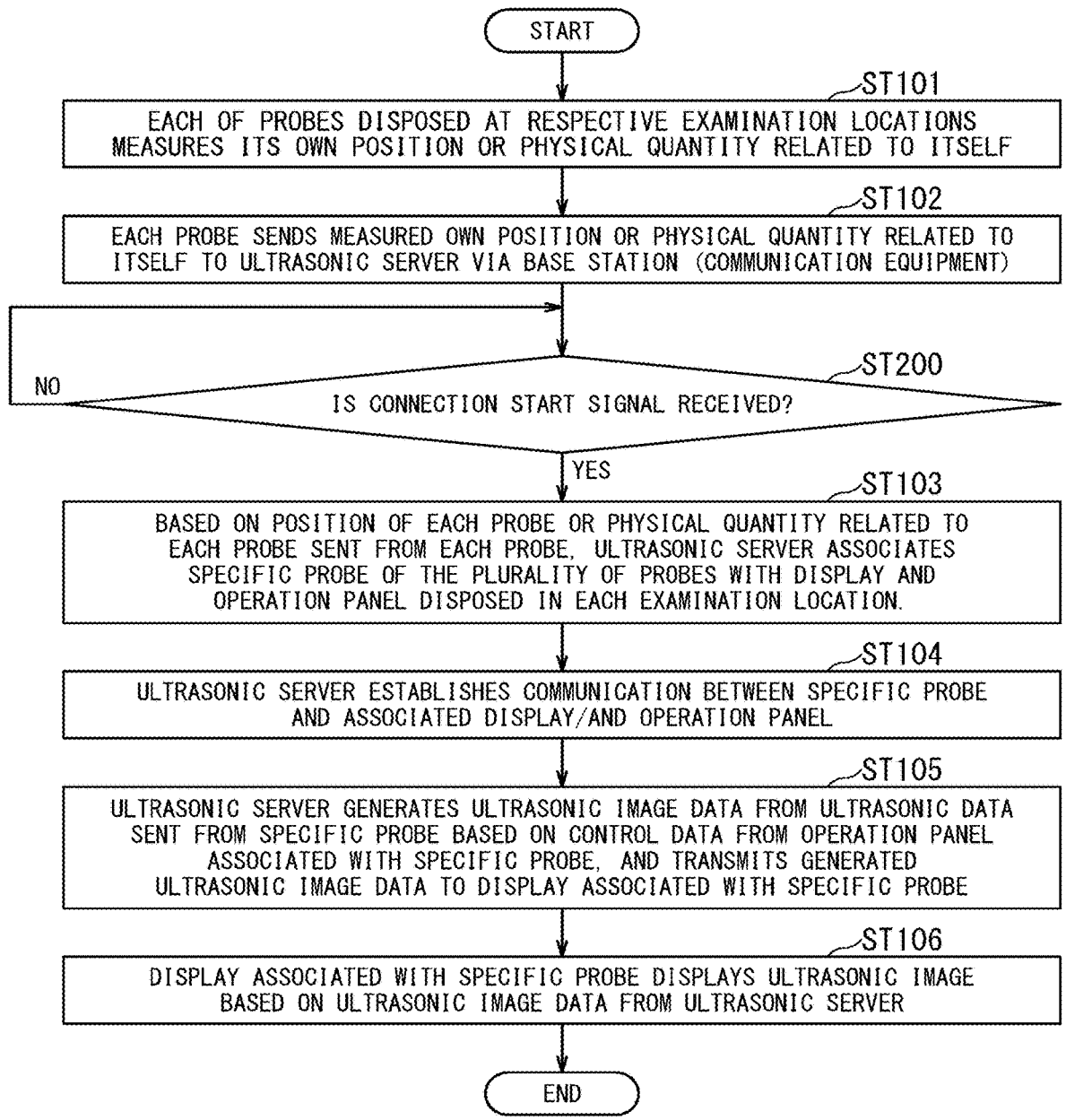
FIG. 5 is a flowchart illustrating processing performed by the ultrasonic diagnostic system according to the first modification of the first embodiment.

FIG. 5 is a flowchart illustrating processing performed by the ultrasonic diagnostic system 1 according to the first modification of the first embodiment. The first modification of the first embodiment differs from the above-described first embodiment (FIG. 4) only in that the processing of the step ST200 is added, while the other processing is the same.

In the step ST200, it is monitored whether or not a connection start signal is inputted from an input interface in response to a manual operation by a user. If the connection start signal is inputted, the processing proceeds to the step ST103. That is, in the step ST200, in response to or in synchronization with input of the connection start signal, the probe 10 closest to the predetermined position is determined as the specific probe 10.

The input interface is, for example, an operation panel 20 installed in the examination location or an appropriate switch provided in each probe 10. At the timing when the user operates the input interface for instructing start of connection, the input interface outputs the connection start signal to the ultrasonic server 50. The processing of the ST200 is performed by the association function 512 of the ultrasonic server 50.

Figure 6:
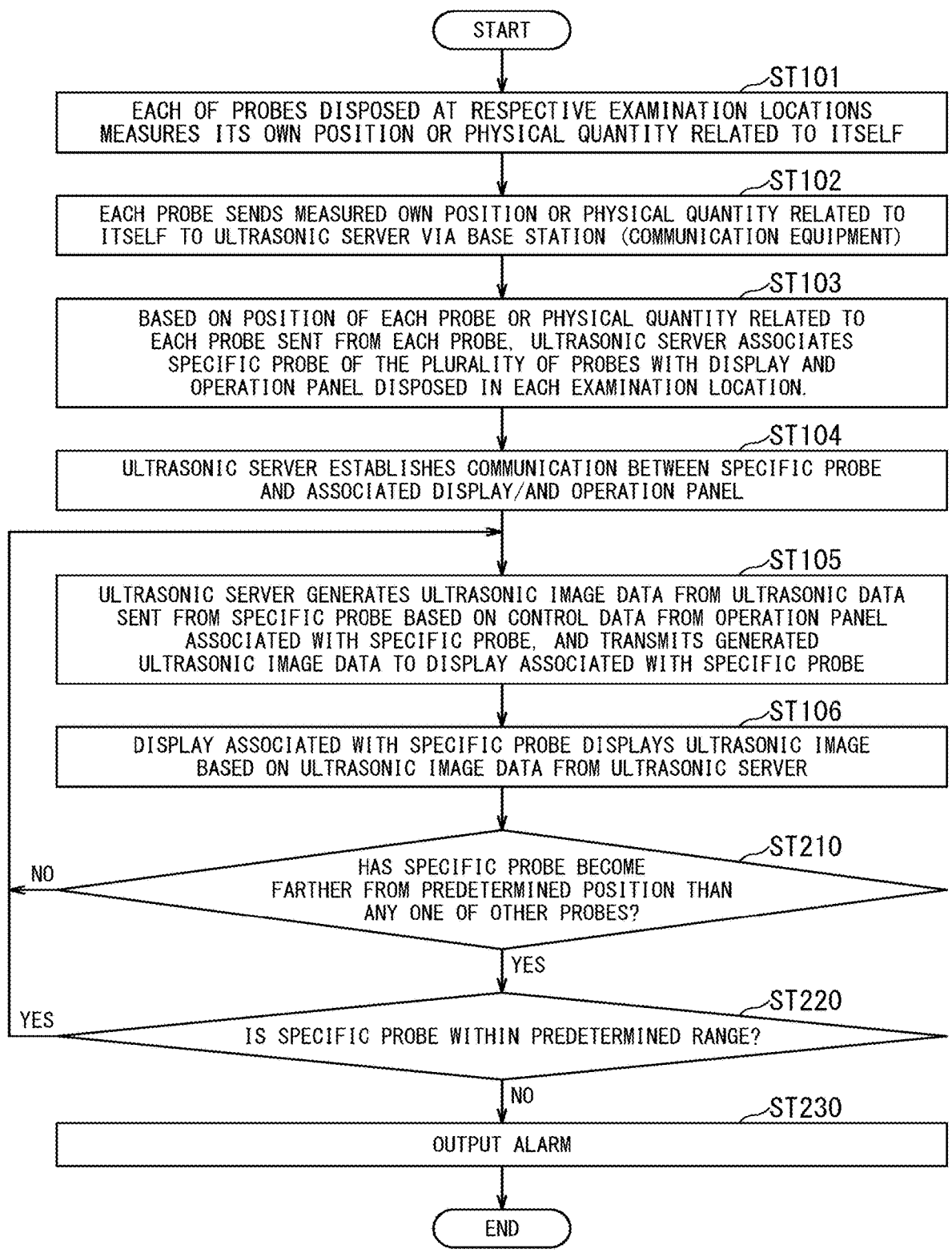
FIG. 6 is a flowchart illustrating processing performed by the ultrasonic diagnostic system according to the second modification of the first embodiment.

FIG. 6 is a flowchart illustrating processing performed by the ultrasonic diagnostic system 1 according to the second modification of the first embodiment. The second modification of the first embodiment differs from the above-described first embodiment (FIG. 4) only in that the processing of the steps ST210, ST220, and ST230 is added, while the other processing is the same.

When each probe 10 is wirelessly connected, the user can move the probe 10 relatively easily. Thus, even when the specific probe 10 and the operation panel 20/the display 22 are once associated with each other, and even when signals are exchanged between the specific probe 10 and the operation panel 20/the display 22, the specific probe 10 can be freely moved by the user. As a result, there is a possibility that the distance between the predetermined position and the once determined specific probe 10 may become longer than that between the predetermined position and one of other probes 10 other than the once determined specific probe 10. In such a case, if the once determined specific probe 10 and the one of other probes 10 are switched according to the determination based on the distance from the predetermined position only, there is a risk that the specific probe 10 and the one of other probes 10 may be frequently switched against the user's intention.

Thus, in the step ST210, even when it is determined that the distance between the predetermined position and the once determined specific probe 10 becomes longer than that between the predetermined position and any one of other probes 10 (YES in the step ST210), as long as the specific probe 10 is within a predetermined range, for example, from the predetermined position (YES in the step ST220), the processing returns to the step ST105 such that the communication and association between the specific probe 10 and the operation panel 20 and display 22 are maintained.

When it is determined in the step ST220 that the specific probe 10 has moved outside the predetermined range (NO in the step ST220), an alarm is generated to notify the user of the situation in the step ST230. In the step ST230, instead of the alarm or in addition to the alarm, the association between the specific probe 10 and the operation panel 20 and the display 22 may be canceled. Alternatively, in the step ST230, the association function 512 may update the association, i.e., may newly associate the operation panel 20 and the display 22 with one of the other probes 10 that is within the predetermined range and closest to the predetermined position among the other probes 10 in place of the current specific probe 10.

Second Embodiment

In the ultrasonic diagnostic system 1 of the first embodiment described above, it is assumed that each of the plurality of probes 10 can be moved from one examination location to another examination location, while operation/display panel 30 composed of the display 22 and the operation panel 20 is fixed at a predetermined examination location. In the ultrasonic diagnostic system 1 of the second embodiment, it is assumed that not only each of the plurality of probes 10 but also each of the plurality of operation/display panels 30 can be moved from one examination location to another examination location.

Each operation/display panel 30 in the ultrasonic diagnostic system 1 of the second embodiment is configured as a portable display terminal 60 that can be easily carried like a tablet terminal, for example. Each portable display terminal 60 includes a touch panel display which can display ultrasonic images and with which various operation data can be inputted.

Figure 7:
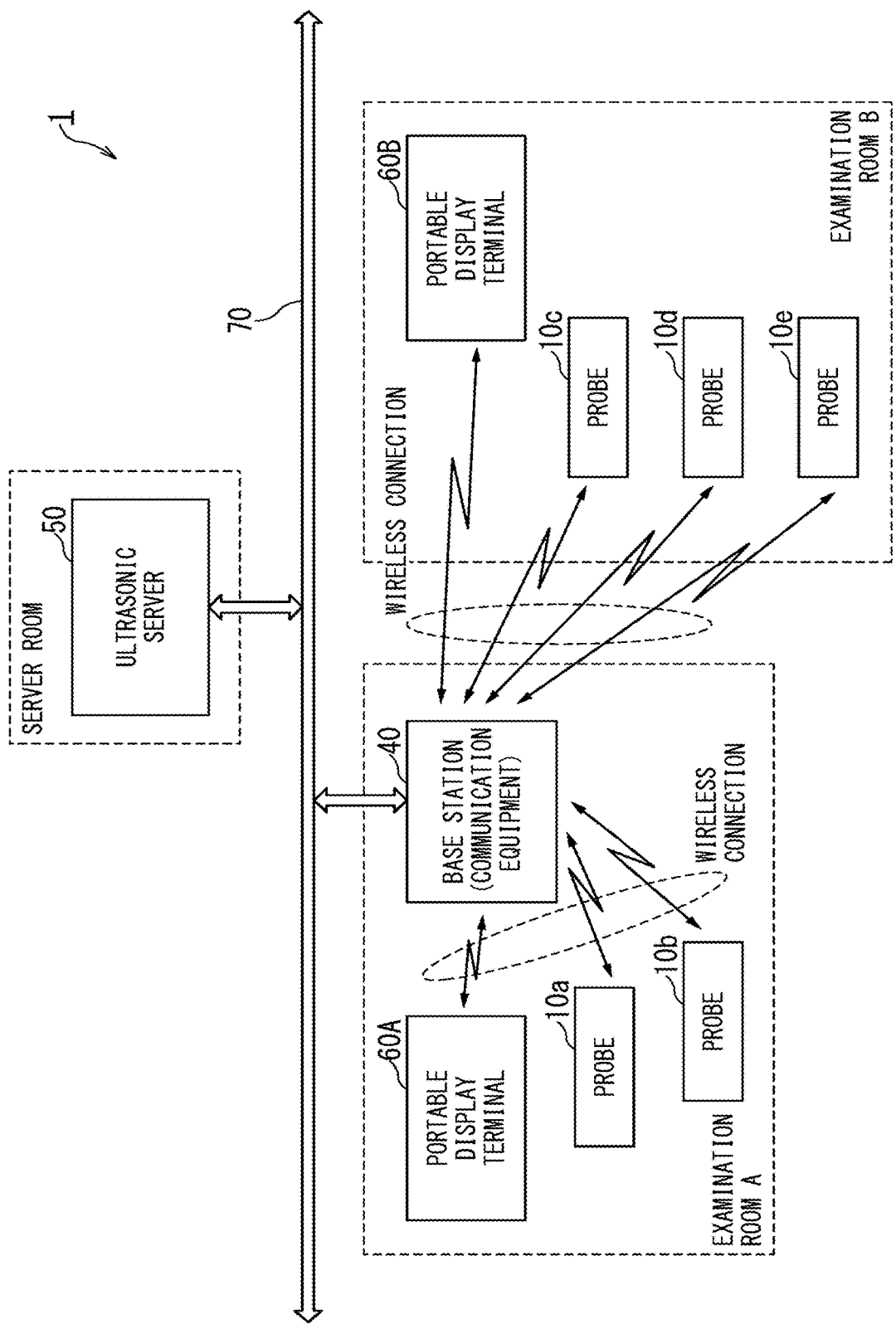
FIG. 7 is a schematic diagram illustrating a system configuration of the ultrasonic diagnostic system according to the second embodiment.

FIG. 7 is a schematic diagram illustrating a system configuration of the ultrasonic diagnostic system 1 according to the second embodiment. The second embodiment differs from the first embodiment in the following two points. Firstly, in the second embodiment, each operation/display panel 30 composed of the operation panel 20 and the display 22 in the first embodiment is replaced by the portable display terminal 60. Secondly, while the operation panels 20 and displays 22 are connected to the network 70 by wire in the first embodiment, the portable display terminals 60 are wirelessly connected to the base station 40 (i.e., communication equipment 40) in the second embodiment.

In the case shown in FIG. 7, the portable display terminal 60A is disposed in the examination room A and the portable display terminal 60B is disposed in the examination room B. However, as described above, each portable display terminal 60 can be easily carried to another location by the user. Thus, in some cases, the portable display terminal 60A may be disposed in examination room B while the portable display terminal 60B may be disposed in the examination room A, or both portable display terminals 60A and 60B may be disposed in either one of the examination rooms A and B.

Figure 8:
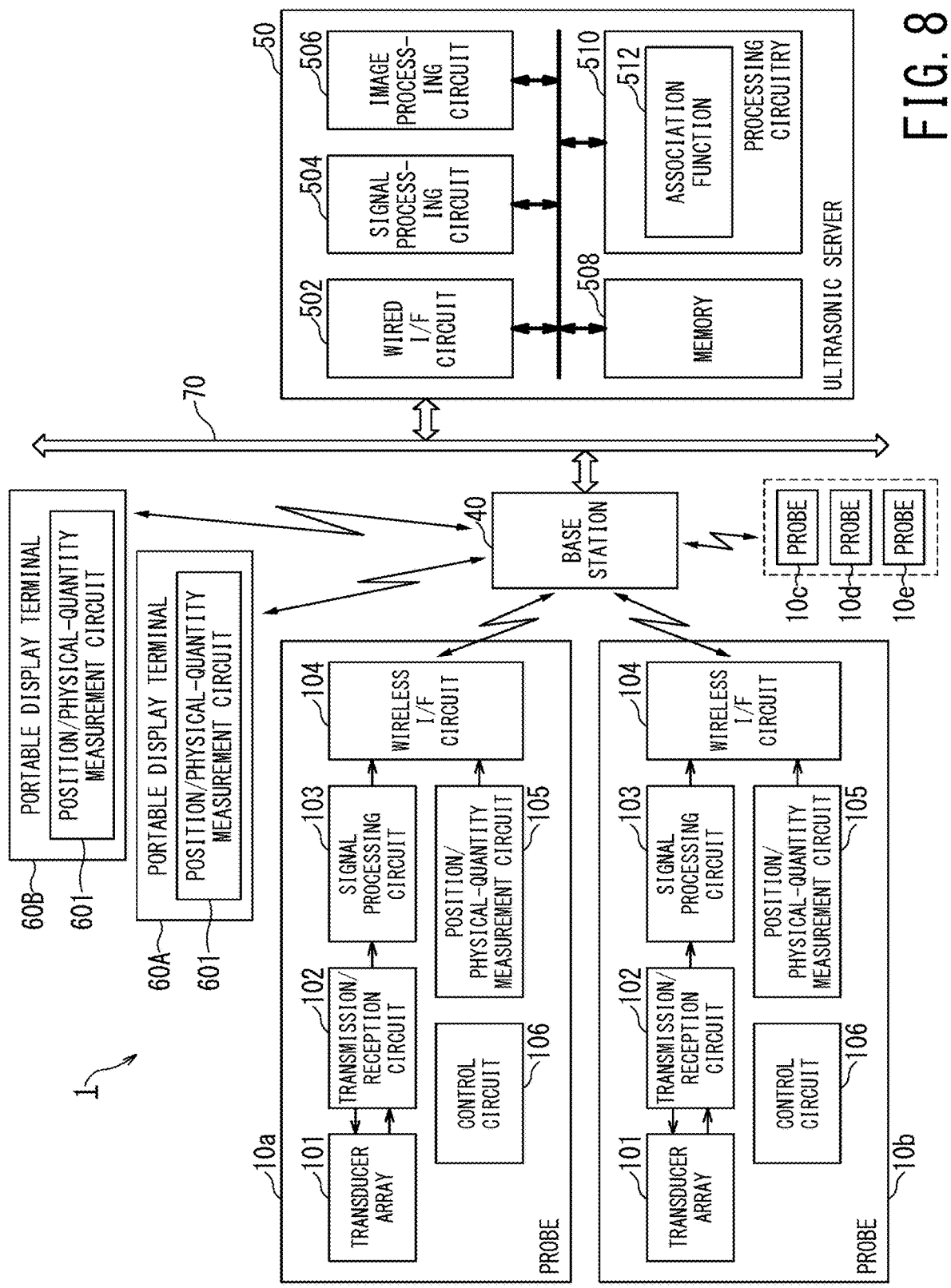
FIG. 8 is a block diagram illustrating a functional configuration of the ultrasonic diagnostic system according to the second embodiment.

FIG. 8 is a block diagram illustrating a functional configuration of the ultrasonic diagnostic system 1 according to the second embodiment. In FIG. 8, all the components except the portable display terminals 60 are the same as those in the first embodiment (FIG. 3).

Each portable display terminal 60 includes a position/physical quantity measurement circuit 601 in addition to the above-described touch panel display which can display ultrasonic images and with which various operation data can be inputted. The function and configuration of the position/physical-quantity measurement circuit 601 are the same as those of the position/physical-quantity measurement circuit 105 included in each probe 10, and thus duplicate description is omitted.

Figure 9:
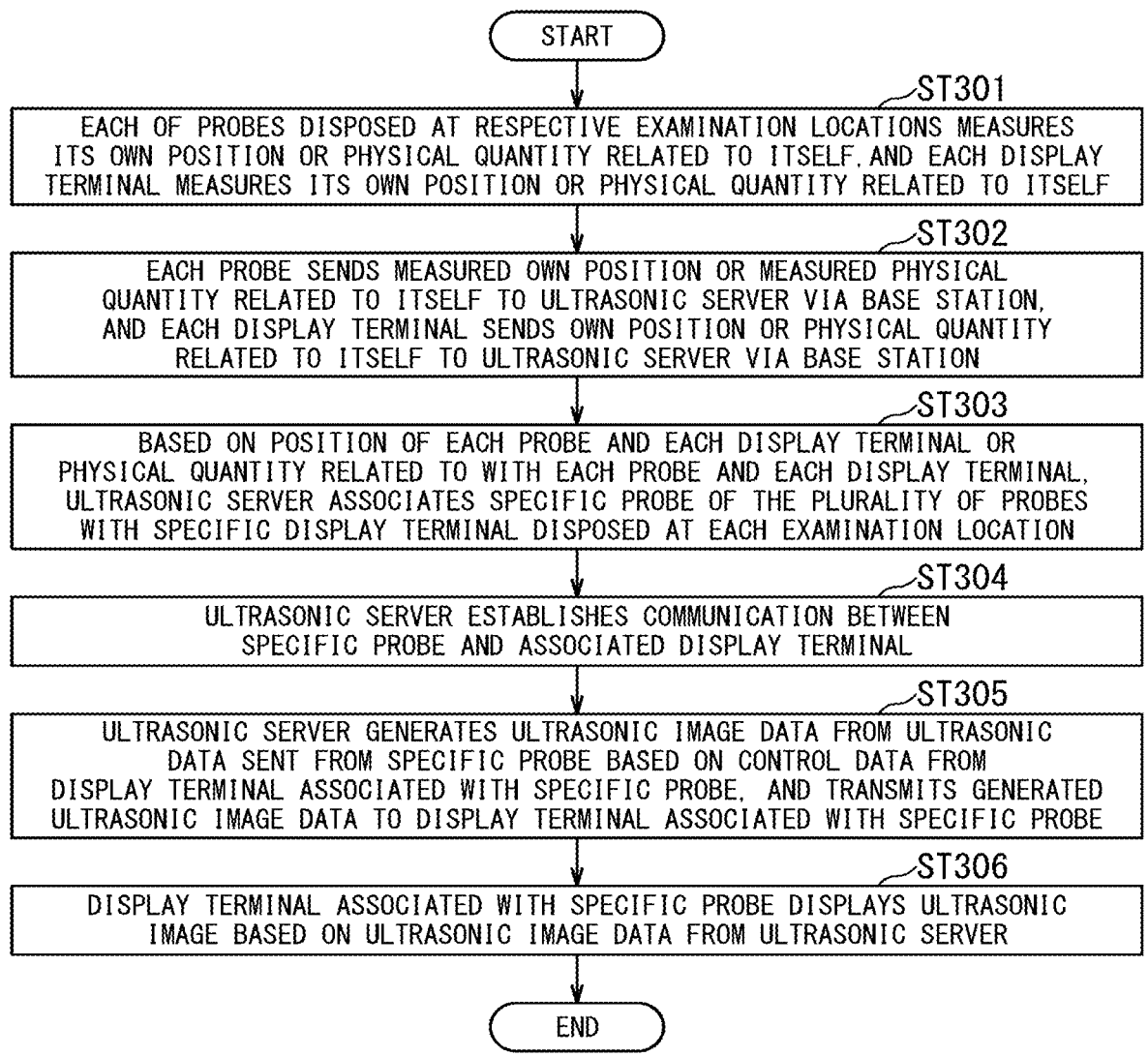
FIG. 9 is a flowchart illustrating processing performed by the ultrasonic diagnostic system according to the second embodiment.

FIG. 9 is a flowchart illustrating processing performed by the ultrasonic diagnostic system 1 of the second embodiment, particularly focusing on the processing of associating one specific probe 10 with one specific portable display terminal 60.

First, in the step ST301, each of the plurality of probes 10 disposed in each examination location measures its own position or the physical quantity related to itself, and each of the portable display terminals 60 measures its own position or the physical quantity related to itself.

Similar to the first embodiment, each probe 10 uses its built-in position/physical-quantity measurement circuit 105 for measuring its own position or the physical quantity related to itself. Meanwhile, each portable display terminal 60 also uses its built-in position/physical-quantity measurement circuit 605 for measuring its own position or the physical quantity related to itself, for example.

The meaning of the position of each portable display terminal 60 and the meaning of the physical quantity related to each portable display terminals 60 are substantially the same as those of each probe 10 in the first embodiment, and thus, duplicate description is omitted. Similarly, the methods of measuring the position of each portable display terminal 60 and the physical quantity related to each portable display terminal 60 are substantially the same as those of each probe 10 in the first embodiment, and thus, duplicate description is also omitted.

In the next step ST302, each probe 10 sends the measured own position information or the measured physical quantity related to itself to the ultrasonic server 50 via the base station 40, and each portable display terminal 60 sends the measured own position information or the measured physical quantity related to itself to the ultrasonic server 50 via the base station 40.

In the next step ST303, based on the location of each probe 10 and each portable display terminal 60, or the physical quantity related to each probe 10 and each portable display terminal 60, which have been sent from each probe 10 and each portable display terminal 60, the ultrasonic server 50 associates one specific probe 10 among the plurality of probes 10 with one specific portable display terminal 60 among the plurality of portable display terminals 60.

The processing of the step ST303 is performed by the association function 512 of the ultrasonic server 50. The association function 512 determines one specific portable display terminal 60 from the plurality of portable display terminals 60, by using the same method as those for determining one specific probe 10 from the plurality of probes 10. For example, the portable display terminal 60 closest to the predetermined position in the examination room can be determined as the specific portable display terminal 60.

In the next step ST304, the association function 512 of the ultrasonic server 50 establishes communication between the specific probe 10 and the specific portable display terminal 60 that are associated with each other.

In the next step ST305, the ultrasonic server 50 generates the ultrasonic image data from the ultrasonic data sent from the specific probe 10, using the control data sent from the specific portable display terminal 60 associated with the specific probe 10. Then, the ultrasonic server 50 transmits the generated ultrasonic image data to the specific portable display terminal 60 associated with the specific probe 10.

In the next step ST306, the ultrasonic server 50 causes the specific portable display terminal 60 associated with the specific probe 10 to display the ultrasonic image based on the ultrasonic image data.

(Modification of Second Embodiment)

Figure 10:
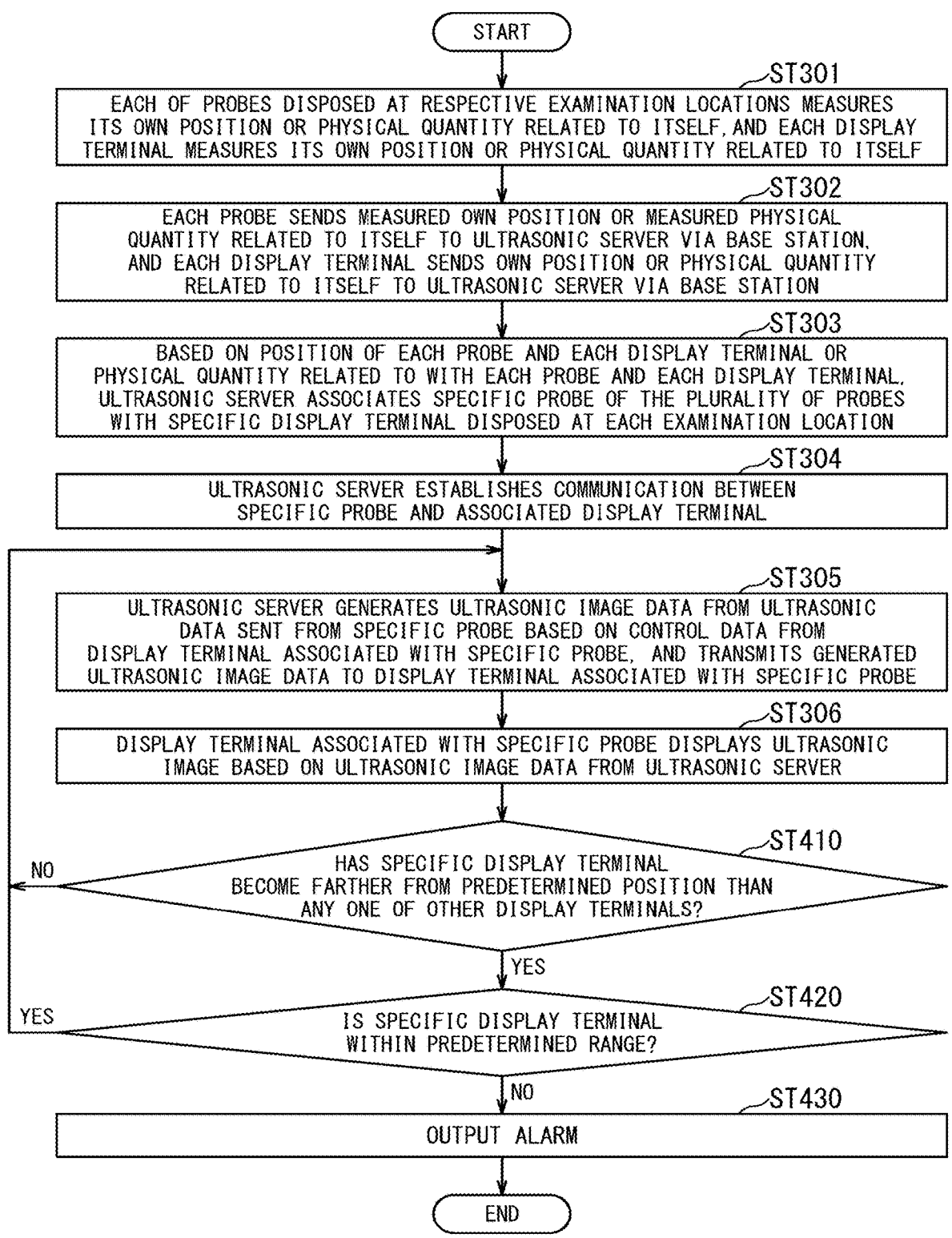
FIG. 10 is a flowchart illustrating processing performed by the ultrasonic diagnostic system according to a modification of the second embodiment.

FIG. 10 is a flowchart illustrating processing performed by the ultrasonic diagnostic system according to a modification of the second embodiment. The modification of the second embodiment differs from the above-described second embodiment (FIG. 9) only in that the processing of the steps ST410 to ST430 are added, while the other processing is the same.

Since the portable display terminals 60 are wirelessly connected, the user can readily move the portable display terminals 60. Thus, even when the specific probe 10 and the specific portable display terminal 60 are once associated with each other and signals are exchanged between the specific probe 10 and the specific portable display terminal 60 via the ultrasonic server 50, the specific portable display terminal 60 can be moved.

As a result, there is a possibility that the distance between the predetermined position and the once determined specific portable display terminal 60 may become longer than that between the predetermined position and the other portable display terminals 60 other than the specific portable display terminal 60. In such a case, if the once determined specific portable display terminal 60 and the other one of the portable display terminals 60 are switched according to the determination based on the distance from the predetermined position only, there is a risk that the specific portable display terminal 60 and the other one of portable display terminals 60 may be frequently switched against the user's intention, similarly to the situations with the probe 10.

Thus, in the step ST410, even when it is determined that the distance between the predetermined position and the once determined specific portable display terminal 60 becomes longer than that of other portable display terminals 60 (YES in the step ST410), as long as the specific portable display terminal 60 is within a predetermined range (YES in the step ST420), the processing returns to the step ST305 such that the communication and association between the specific probe 10 and the specific portable display terminal 60 are maintained.

In the next step ST420, when it is determined that the specific portable display terminal 60 has moved outside the predetermined range (NO in the step ST420), an alarm is issued to notify the user of that situation in the step ST430. In the step ST430, instead of the alarm or in addition to the alarm, the association between the specific probe 10 and the specific portable display terminal 60 may be canceled, similarly to the second modification of the first embodiment. Alternatively, in the step ST430, the association function 512 may update the association, i.e., may newly associate the specific probe 10 with one of the other portable display terminals 60 that is within the predetermined range and closest to the predetermined position among the other portable display terminals 60.

Third Embodiment

Figure 11:
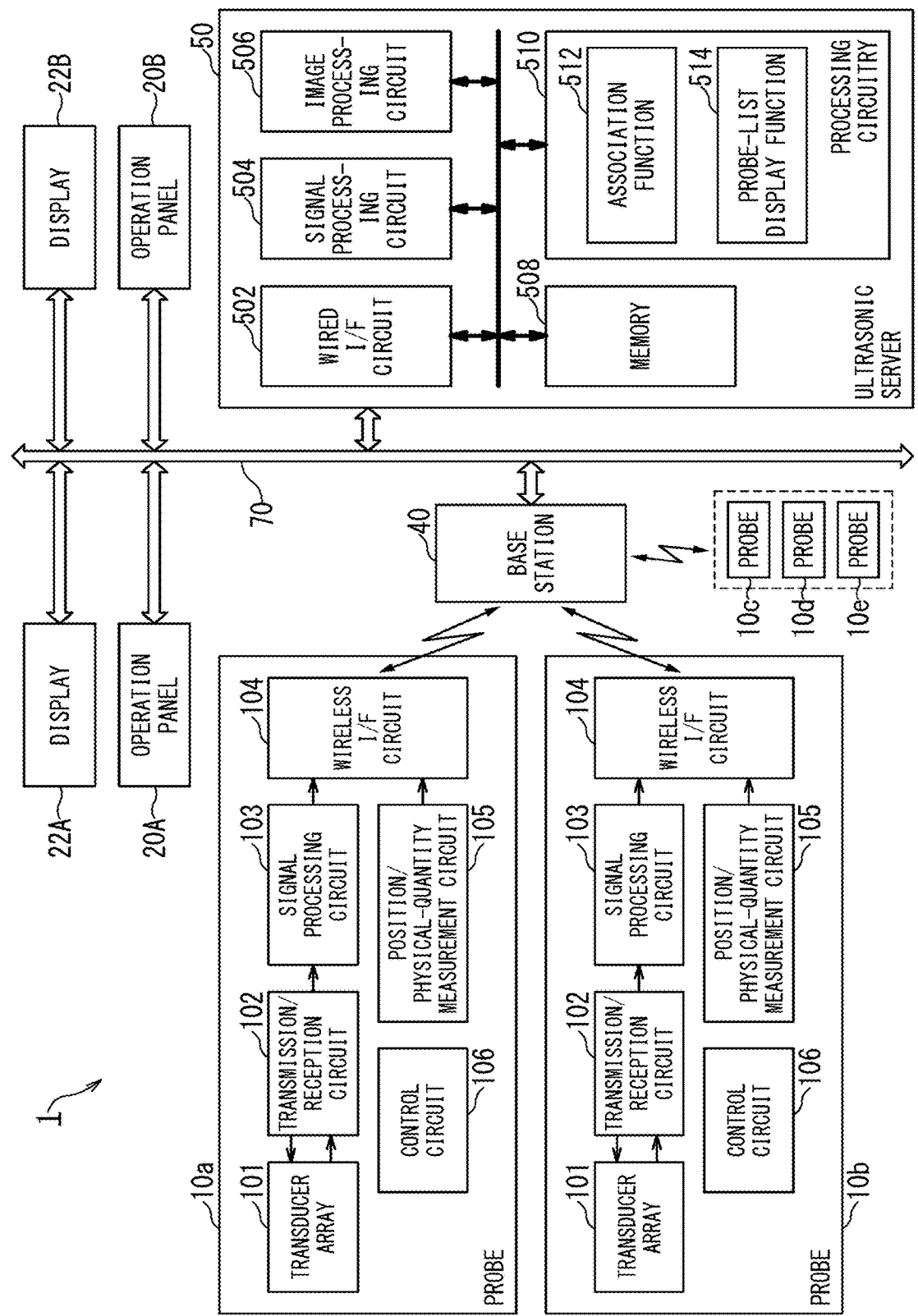
FIG. 11 is a block diagram illustrating a functional configuration of the ultrasonic diagnostic system according to the third embodiment.

FIG. 11 is a block diagram illustrating a functional configuration of the ultrasonic diagnostic system 1 according to the third embodiment. The third embodiment differs from the first embodiment (FIG. 3) in that the processing circuitry 510 of the ultrasonic server 50 further has a probe-list display function 514.

For example, in the first modification of the first embodiment, the user operates the operation panel 20 installed in the examination location (for example, the operation panel 20A installed in the examination room A) to give an instruction to start the examination by, for example, transmitting a connection start command. When the instruction to start the examination is given, the specific probe 10 is determined on the basis of the distance between the predetermined position and the respective probes 10, and then, the specific probe 10 is connected to the operation panel 20A and the display 22A.

In some cases, the user may want to know information about the connectability and/or connection priority status of each of the plurality of probes 10, and then select the specific probe 10 to be connected to the operation panel 20A and display 22A from the plurality of probes 10, based on the information about the connectability and connection priority status. In the third embodiment, information for supporting such probe selection is displayed as, for example, a probe list on the display 22A.

Figure 12:
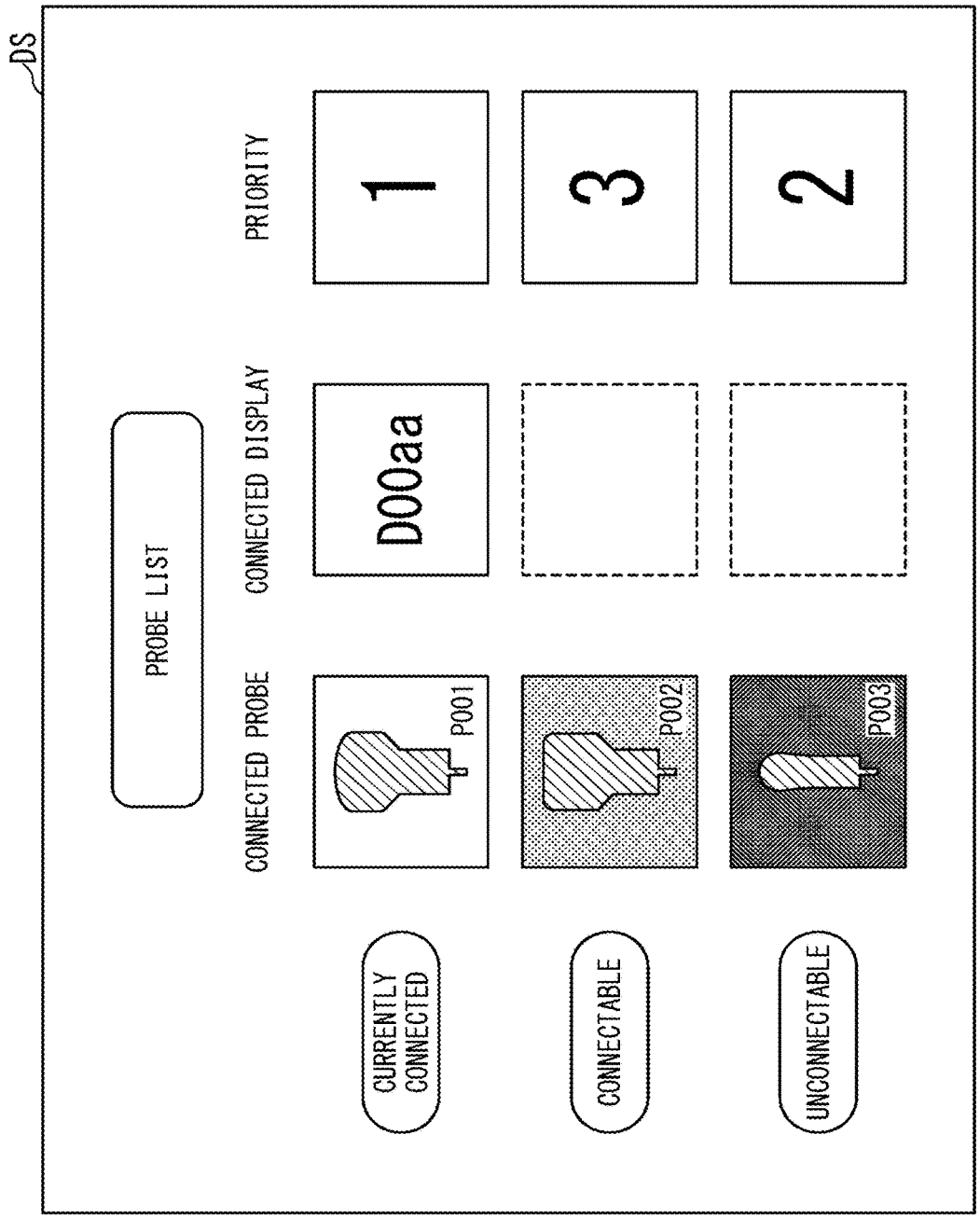
FIG. 12 is a schematic diagram illustrating a probe list displayed on a display.

FIG. 12 is a schematic diagram illustrating a probe list displayed on a probe-list screen DS. The probe list shows connection status of the probes 10 related to the predetermined examination room in which the ultrasonic diagnostic system 1 is used.

For example, a probe list showing the connection status of the probes related to examination room A is included in a probe-list screen DS, and this probe-list screen DS appears on the display 22A installed in the examination room A. In this case, for example, when a switch or button of the operation panel 20A installed also in the examination room A is pressed, the probe-list screen DS appears on the display 22A. When the operation panel 20A is provided with a touch panel screen, the probe-list screen DS may be displayed on the touch panel screen.

For example, the probe list includes: a column of "connected probes" showing the probe connection status with the probe icons; a column of "connected display" showing the display to which a probe is connected; and a column of "priority" showing connection priority of the probes.

The probe icons displayed in the column of "connected probes" schematically indicates the shape of each probe to be connected, and the identification information of the probe, for example, "P001" is displayed at the lower right of the probe shape. The probe icons are shown with different backgrounds, and the brightness of the background enables to tell the connection status of each probe at a glance. The connection status of each probe can be represented by, for example, "highlight display" with the brightest background, "normal display" with a medium-degree brightness background, and "gray down display" with the darkest background.

For example, the "highlight display" indicates that the probe is currently connected to the display 22A. The "normal display" indicates that the probe is currently connectable, while the currently connected probe is excluded from the "normal display". The "gray down display" indicates that the probe is currently unconnectable.

The connectability of each probe is determined on the basis of at least one of the five points as follows: (a) whether or not the each probe is connected to one of other displays other than the display (for example, the display 22A) displaying the probe list; (b) diagnosis status and communication status related to the each probe; (c) battery charging status of the each probe; (d) the distance between the predetermined position and the each probe, and (e) whether or not the each probe is within the predetermined range. The determination regarding the connectability may be performed by, for example, the probe-list display function 514 of the ultrasonic server 50.

Note that the diagnosis status is information indicating what kind of diagnosis is to be performed, and the diagnosis status eventually becomes information about a required communication speed of the probe. Specifically, the diagnosis status may include the anatomical part of the object to be examined, the imaging mode such as the B-mode method and the color Doppler method, the imaging conditions such as the frame rate, and information on the contents of the examinations such as contrast-enhanced examination or non-contrast examination. Depending on the diagnosis status, the required communication speed of the probe necessary for performing the diagnosis may differ.

The communication status means the maximum communication speed that the probe can currently achieve. The connectability of the probe can be determined by comparing the diagnosis status (e., g., the required communication speed of the probe) with the communication status (e., g., the maximum communication speed that can be achieved).

The column of "connected display" shows the identification information of the display to which each probe 10 is currently connected. When an icon in the "connected probe" column is displayed in "highlight", the identification information of the corresponding connected display (for example, "D00aa") is shown in the same row in the "connected display" column.

In the column of "priority", a number indicating the connection priority of the probes 10 is displayed. The connection priority is preset for each probe 10 managed by the ultrasonic server 50, and such connection priority data is stored in the memory 508 by the ultrasonic server 50 in advance.

The connection priority may be set by the user, or the ultrasonic server 50 may automatically set the connection priority, based on data (e. g., a lookup table) that associates the connection priority with the identification information of the probes 10 and/or the diagnosis status.

As described above, the diagnosis status is information indicating what kind of diagnosis is performed. The diagnosis status, for example, may be information including the contents of the examination such as contrast-enhanced examination or non-contrast examination. For example, in an examination with a high diagnostic cost such as contrast-enhanced examination, it is desirable to give higher connection priority to the probe used for the contrast-enhanced examination.

The connection priority having been set in this manner is displayed in the "priority" column of the probe list. The user can check the connection status of each probe by referring to the probe list displayed on the display 22. Further, the user can select the probe to be used by using the probe selection button provided on the operation panel 20 while looking at the probe list, for example.

The functions other than displaying information in the probe list can be achieved on the basis of the connection priority. For example, when there are two or more probes connected to the base station 40, a function of preferentially securing a transfer rate for a probe having higher priority can be achieved.

Further, the probe-list display function 514 of the ultrasonic server 50 may additionally display, in the probe list, data related to the distance between the predetermined position and each probe, or the position information of each probe.

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

What is claimed is:

1. An ultrasonic diagnostic system, comprising:
   a plurality of probes;
   at least one operation/display panel configured to be disposed at a same examination location as at least one of the plurality of probes;
   communication equipment configured to communicate with the plurality of probes;
   processing circuitry configured to determine a probe closest to a predetermined position in the examination location as a specific probe among the plurality of probes and associate the specific probe with the operation/display panel; and
   an ultrasonic server configured to be disposed at a location different from the examination location, receive first data acquired by the specific probe via the communication equipment, generate second data based on the first data, and transmit the second data to the operation/display panel via the communication equipment.

2. The ultrasonic diagnostic system according to claim 1, wherein the predetermined position is a position of the operation/display panel, a position of an object at the examination location, or a specific position on a bed in the examination location.

3. The ultrasonic diagnostic system according to claim 1, further comprising a measurement circuit configured to detect respective positions of the plurality of probes, wherein:
the processing circuitry is further configured to determine the probe closest to the predetermined position in the examination location as the specific probe based on respective distances between the plurality of probes and the predetermined position.

4. The ultrasonic diagnostic system according to claim 3, wherein, once the specific probe and the operation/display panel are associated with each other, the processing circuitry is further configured to maintain the association between the specific probe and the operation/display panel even when a distance between the specific probe and the predetermined position becomes longer than a distance between one of other probes of the plurality of probes and the predetermined position.

5. The ultrasonic diagnostic system according to claim 1, wherein:
the processing circuitry is further configured to set a predetermined range around the predetermined position; and
when the specific probe moves outside the predetermined range, the processing circuitry is further configured to perform at least one of: (a) canceling the association between the specific probe and the operation/display panel; (b) updating the association by newly associating the operation/display panel with one of other probes of the plurality of probes within the predetermined range other than a current specific probe; and (c) issuing an alarm.

6. The ultrasonic diagnostic system according to claim 1, further comprising an input interface configured to output a connection start signal that instructs start of connection,
wherein the processing circuitry is further configured to determine the probe closest to the predetermined position as the specific probe, when the connection start signal is output.

7. The ultrasonic diagnostic system according to claim 1, further comprising a second measurement circuit, wherein:
the at least one operation/display panel is a plurality of portable operation/display panels configured to be portable; and
the second measurement circuit is configured to measure a second physical quantity related to the plurality of portable operation/display panels;
the processing circuitry is further configured to associate a specific portable operation/display panel of the plurality of portable operation/display panels with the specific probe based on the second physical quantity; and
the ultrasonic server is further configured to transmit the second data to the specific portable operation/display panel via the communication equipment.

8. The ultrasonic diagnostic system according to claim 7, wherein;
the second measurement circuit is configured to detect respective positions of the plurality of portable operation/display panels; and
the processing circuitry is further configured to determine a portable operation/display panel closest to the predetermined position in the examination location as the specific portable operation/display, based on respective distances between the plurality of portable operation/display panels and the predetermined position.

9. The ultrasonic diagnostic system according to claim 8, wherein, after once the specific portable operation/display panel and the specific probe are associated with each other, the processing circuitry is further configured to maintain the association between the specific portable operation/display panel and the specific probe even when a distance between the specific portable operation/display panel and the predetermined position becomes longer than a distance between one of other portable operation/display panels and the predetermined position.

10. The ultrasonic diagnostic system according to claim 7, wherein the processing circuitry is further configured to set a second predetermined range around the predetermined position; and,
when the specific portable operation/display panel moves outside the second redetermined range, the processing circuitry is further configured to perform at least one of: (a) canceling the association between the specific portable operation/display panel and the specific probe; (b) updating the association by newly associating the specific probe with one of other portable operation/display panels within the second predetermined range other than a current specific portable operation/display panel; and (c) issuing an alarm.

11. The ultrasonic diagnostic system according to claim 7, wherein the plurality of portable operation/display panels are configured to wirelessly communicate with the communication equipment.

12. The ultrasonic diagnostic system according to claim 1, wherein the plurality of probes are configured to wirelessly communicate with the communication equipment.

13. The ultrasonic diagnostic system according to claim 1, wherein:
the at least one operation/display panel comprises an operation/display panel disposed at the examination location and one or more other operation/display panel disposed in a different examination location; and
the ultrasonic server is further configured to cause the operation/display panel disposed at the examination location to display a probe list that contains a probe connected to the operation/display panel, a probe connectable to the operation/display panel, and a probe connected to the one or more other operation/display panel.

14. The ultrasonic diagnostic system according to claim 13, wherein:
the probe list contains information indicating connectability with each probe in the probe list; and
the ultrasonic server is further configured to determine the connectability of the each probe based on at least one of (a) whether or not the each probe is connected to a display other than the operation/display panel; (b) a diagnosis status and a communication status related to the each probe; (c) a battery charging status of the each probe; (d) a distance between the predetermined position and the each probe, and (e) whether or not the each probe is within the predetermined range.

15. The ultrasonic diagnostic system according to claim 13, wherein:
the probe list contains information indicating connection priority of the plurality of probes; and
the connection priority is set by a user.

16. The ultrasonic diagnostic system according to claim 15, wherein the ultrasonic server preferentially secures a transfer rate for a probe having a higher connection priority when two or more probes perform communication via the communication equipment.

17. The ultrasonic diagnostic system according to claim 13, wherein:
the probe list contains information indicating a connection priority of the plurality of probes; and
the ultrasonic server is further configured to set the connection priority based on data in which at least one of identification information and the diagnostic status of each probe is associated with the connection priority.

18. The ultrasonic diagnostic system according to claim 13, wherein the probe list contains position information of the plurality of probes.

19. An ultrasonic diagnostic system, comprising:
a plurality of probes;
at least one operation/display panel configured to be disposed at a same examination location as at least one of the plurality of probes;
communication equipment configured to communicate with the plurality of probes;
processing circuitry configured to associate a specific probe of the plurality of probes with the operation/display panel; and
an ultrasonic server configured to be disposed at a location different from the examination location, receive first data acquired by the specific probe via the communication equipment, generate second data based on the first data, and transmit the second data to the operation/display panel via the communication equipment,
wherein, the ultrasonic server is further configured to cause the operation/display panel to display a probe list that contains the specific probe connected to the operation/display panel in association with the operation/display panel and a probe connectable to the operation/display panel.

* * * * *